(12) United States Patent
Weekamp et al.

(10) Patent No.: US 9,675,265 B2
(45) Date of Patent: Jun. 13, 2017

(54) FEEDING TUBE

(75) Inventors: Johannes Wilhelmus Weekamp, Beek en Donk (NL); Johannes Herman Savenije, Eindhoven (NL); Aaldert Elevelt, Best (NL); Marcus Jozef Van Bommel, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1808 days.

(21) Appl. No.: 12/518,278

(22) PCT Filed: Dec. 7, 2007

(86) PCT No.: PCT/IB2007/054968
§ 371 (c)(1),
(2), (4) Date: Jun. 9, 2009

(87) PCT Pub. No.: WO2008/072150
PCT Pub. Date: Jun. 19, 2008

(65) Prior Publication Data
US 2010/0036229 A1   Feb. 11, 2010

(30) Foreign Application Priority Data
Dec. 13, 2006   (EP) .................................. 06126039

(51) Int. Cl.
*A61B 5/04*  (2006.01)
*A61B 5/042*  (2006.01)
*A61J 15/00*  (2006.01)

(52) U.S. Cl.
CPC ......... *A61B 5/0421* (2013.01); *A61J 15/0003* (2013.01); *A61J 15/0073* (2013.01); *A61J 15/0084* (2015.05)

(58) Field of Classification Search
USPC ........... 600/374, 380, 381, 393, 509; 29/825
See application file for complete search history.

(56) References Cited

U.S. PATENT DOCUMENTS

| | | | |
|---|---|---|---|
| 4,574,807 A * | 3/1986 | Hewson et al. | 607/27 |
| 4,592,372 A * | 6/1986 | Beranek | 607/119 |
| 4,644,957 A | 2/1987 | Ricciardelli et al. | |
| 4,921,481 A * | 5/1990 | Danis et al. | 604/67 |
| 5,334,167 A | 8/1994 | Cocanower | |
| 5,409,652 A | 4/1995 | Carter | |

(Continued)

FOREIGN PATENT DOCUMENTS

| EP | 0004785 A1 | 10/1979 |
|---|---|---|
| EP | 0334086 A2 | 9/1989 |

(Continued)

*Primary Examiner* — Lee S Cohen
*Assistant Examiner* — Erin M Cardinal

(57) ABSTRACT

The invention is related to a feeding tube (1, 11, 15) in particular for total parental nutrition and/or medicine dosing including at least one inner tubing (9), at least one lumen (2, 13), at least one sensing element, in particular an electrode (3), the sensing element being connected to at least one monitoring device by a wiring (4, 12, 17) for internal monitoring of a patient's vital functions. The wiring (4, 12, 17) is at least partially wounded in tight contact with a surface of the inner tubing (9). Wherein the inner tubing (9) is at least partially surrounded by an outer tubing (8) in order to cover the inner tubing (9) and/or the wiring (4, 12, 17).

9 Claims, 3 Drawing Sheets

(56) References Cited

U.S. PATENT DOCUMENTS

| | | | |
|---|---|---|---|
| 5,476,495 A * | 12/1995 | Kordis et al. | 607/122 |
| 5,591,142 A * | 1/1997 | Van Erp | 604/526 |
| 5,755,687 A * | 5/1998 | Donlon | 604/508 |
| 6,030,382 A * | 2/2000 | Fleischman et al. | 606/41 |
| 6,078,830 A * | 6/2000 | Levin et al. | 600/374 |
| 6,856,822 B2 | 2/2005 | Larsson | |
| 7,149,585 B2 * | 12/2006 | Wessman et al. | 607/116 |
| 2002/0143377 A1 * | 10/2002 | Wessman et al. | 607/116 |
| 2005/0159659 A1 * | 7/2005 | Sawan et al. | 600/380 |
| 2007/0213611 A1 * | 9/2007 | Simpson et al. | 600/365 |
| 2008/0125638 A1 * | 5/2008 | Sinderby et al. | 600/373 |
| 2008/0249507 A1 * | 10/2008 | Hadani | 604/523 |
| 2010/0059173 A1 * | 3/2010 | Kampa et al. | 156/244.15 |
| 2011/0245647 A1 * | 10/2011 | Stanislaus et al. | 600/380 |

FOREIGN PATENT DOCUMENTS

| | | | | |
|---|---|---|---|---|
| EP | 0617916 A1 | 10/1994 | | |
| EP | 0920850 A2 | 6/1999 | | |
| GB | 2254253 A * | 10/1992 | ............ | A61B 5/042 |
| GB | 2397231 A | 7/2004 | | |
| JP | 06335460 A | 12/1994 | | |
| WO | 9217150 A1 | 10/1992 | | |
| WO | 0062851 A1 | 10/2000 | | |
| WO | 0152740 A1 | 7/2001 | | |
| WO | 2004065098 A1 | 8/2004 | | |
| WO | 2006015230 A2 | 2/2006 | | |
| WO | 2006060458 A1 | 6/2006 | | |
| WO | WO 2006060458 A1 * | 6/2006 | | |
| WO | 2006074557 A1 | 7/2006 | | |

* cited by examiner

FEEDING TUBE

The present invention is directed to a feeding tube in particular for total parenteral nutrition and/or medicine dosing including at least one inner tubing, at least one lumen, at least one sensor element, in particular an electrode, the sensing element being connected to at least one monitoring device by a wiring for internal monitoring of a patient's vital functions, the wiring being at least partially wound in tight contact with a surface of the inner tubing.

In hospitals many vital functions, such as ECG, pO2, respiratory motion, etc, are measured to monitor patients. Traditionally, this is done using detectors, such as electrodes on the outside of the patient. Oesophageal physiological monitoring offers an advantage in terms of the reliability and accuracy of signals. For Intensive care patients and immature babies a feeding tube is often needed to feed and to provide medicine. In case of premature neonates even more than 90% of these neonates in Intensive care are very immature and are therefore fed by feeding tubes. Sensors for detecting and recording the above functions can be combined with the oesophageal feeding tube or a catheter.

For intensive care patient and also for neonatal children there is a need for continuously monitoring the ECG signal for sometimes several weeks. Currently sensors are attached the skin on the chest to record those signals. During handling of the sensors, the skin can be damaged and makes it more susceptible for infections.

Special care must be exercised in handling and monitoring of low birth weight infants which are often very thin and fragile and light weighted. The skin is very sensitive and easily bruised such that superficial damage may occur when a monitor lead is placed on the infant's body for an even short period of time. In addition, skin injury may be caused by tape or electrode adhesives. Survival of many infants requires minimal manipulation or interference to thus prevent unnecessary stress or injury.

Internal monitoring of vital functions offers the advantage not to bruise the patient's skin. The oesophagus is an ideal place to monitor several functions of a patient as it is close to heart and lungs and has a good conduction for electrical signals. Compared to present used monitoring techniques, in which electrodes are attached to the skin, no skin damage will occur, nor do external electrical wires hamper medical therapy and nursing care, if a modified oesophageal feeding tube is used.

A modified feeding tube enables to get a higher accuracy of the signals and to have the ability of measuring parameters, which cannot be determined from the outside. Furthermore, there is no need to have all the wires and sensors on the outside of the patient, which can improve the handling speed of hospital personnel.

A problematic item of such a device is the contacting between the electrical wires and the electrodes. This is often complicated and therefore results in high manufacturing costs. Additionally the wires in the lumen of the feeding tube need to be contacted to an electronic circuit of the measuring device. The use of a soldering procedure to connect the wiring of the electrodes may result in a reliability problem.

To solve this problem, document EP 0 617 916 B1 proposes to provide a feeding tube to be inserted into a patient's esophagus, comprising a continuous wiring system in that a plurality of signal lines is wound in tight contact to a surface of a base tube wherein each of the plurality of signal lines has an electrode and a cladding structure, consisting of at least a conductive wire and also an isolating coating around the conductive wire. In this disclosure each of said plurality of signal lines has a portion at which the isolating coating is stripped off so as to form said electrodes by tightly winding the wire around the tube. The other part of the wiring not building the electrodes and being coated with at least on isolating is spiral-wise wrapped around the feeding tube towards a proximal end thereof. At the proximal end of the feeding tube, the wiring has a second insulating which has the function to give additional mechanical strength to the external wiring to be contacted to the measuring or monitoring device.

The feeding tube according to this disclosure has the following problem. First, the wiring itself is not protected against stress which may be implemented by the outside world, which may lead to a reliability problem. Furthermore the isolating cladding structure is exposed to the environmental conditions which may cause a corrosion of the material being used.

Second, there may arise a problem regarding the compatibility of the materials being used for building the electrodes and or the base tubing in that a patient may be allergic to these materials being particularly suitable. Therefore, the choice of material may be restricted to materials whose risk of an allergic reaction of the patient is low.

It is therefore an object of the present invention to provide a reliable feeding tube which allows every choice of material and a comfortable handling while simultaneously keeping the cost for manufacturing the feeding tube low.

The inner tubing of the feeding tube according to the invention is at least partially surrounded by an outer tubing in order to cover the inner tubing and/or the wiring. With such an outer tubing the wiring is protected against any stress being implemented from the surrounding such as by the oesophagus and/or the positioning and is isolated against the surrounding so that the material of the inner tubing is free from any limitations regarding the material to be chosen. The risk of corroding of the material to be used because of the environmental conditions is also minimized. Furthermore, the outer tubing gives the wiring as well as the inner tubing a better mechanical strength.

To allow an access to the sensing elements in one embodiment at least one opening is provided in the outer tubing at the location of the at least one sensing element. It is to be understood, that the at least one opening may be inserted into the outer tubing before fixing the outer tubing onto the inner tubing if the outer tubing and the inner tubing are build by two separate units. It is also possible to already provide openings in the outer tubing at its manufacturing process.

In one embodiment of the present invention the sensing element is formed by winding a wire in a coil onto the inner tubing. Thus, it is possible to build the wiring and the sensing element from one-piece so that no internal connections between the electrodes and the wiring need to be made ensuring a high reliability of the device. With other words one end of the wiring builds the electrodes wherein the other end of the wiring is connected to the measuring or monitoring equipment. The wiring not building the electrode may further comprise an additional electrical insulating material at the proximal end which gives the wiring additional mechanical strength in a portion to be attached to the measuring or monitoring equipment for example by a connector. It is further possible to enlarge the electrodes by applying an additional electrode at the location of the wound electrode for example by depositing a thin metal film or by applying a high conductive polymer, e.g. by using a filled polymeric material.

It is possible to provide the inner tubing with at least one recess on its surface, that matches with the dimensions of the at least one sensing element and/or the wiring, which allows an easy positioning of the sensing element and/or the wiring at a predetermined location on the inner tubing and ensures that the sensing element and/or the wiring does not shift, which otherwise may lead to a short circuit.

The surface area of the outer tubing may have a slide spiral shape which will enable a much smoother insertion of the feeding tube compared to a completely flat outer surface. This shape may be actively manufactured or may arise due to the close fitting of the inner and the outer tubing enclosing the spiral wise wounded wiring on the inner tubing.

The outer tubing may be a shrinking-wrapped-tube so as to fit the outer tubing onto the inner tubing by shrinking. Alternatively it is also possible to fix the outer tubing to the inner tubing in that the outer tubing has a smaller inner diameter than the outer diameter of the inner tubing wherein for insertion into the outer tubing the inner tubing may be stretched to diminish the outer diameter of the inner tubing temporally ensuring a tight fit after release of the inner tubing.

In one alternative embodiment of the present invention the outer tubing and the inner tubing are made from one-piece wherein at least one inner lumen is formed in the center of the feeding tube and at least one outer lumen is formed near the surface of the one-piece feeding tube for guiding and protecting the wiring to be inserted into the at least one outer lumen.

To make the insertion of the wiring easier and to enable an exchange of the wiring at a later stage at least one groove may be located in the at least one outer lumen which provides a continuous opening in the circumference of the feeding tube. If the material of the feeding tube is flexible the groove in the surface of the feeding tube may be widened by pressing the tube at the outside of the tube for example at a position which is perpendicular to the groove and thereby deforming it.

An easy way of manufacturing the feeding tube according to the invention is to build the inner tubing and/or the outer tubing by injection moulding. The sensing element and the wiring in this case may already be connected to the inner tubing while injection moulding the outer tubing using for example PVC, silicon or other polymeric material appropriate as a medical polymer. Alternatively, the wiring, the sensing element and/or contacts may be already inserted into the mould before injection moulding the tubing material.

If the feeding tube is build by two separate tubings, a second material may be used for the moulding of the connector which connects the wiring to the external measuring or monitoring equipment.

The use of injection moulding as the manufacturing method of the feeding tube enables the integration of the sensing element at the distal end of the feeding tube, the use of very thin wiring because no isolation is needed—but can be applied if desired—and the integration of the contacts to the measurement equipment in the feeding connector. Therefore, an optimized distal end of the feeding tube which is smoother is provided. Thus it prevents a possible harming of the patient due to sharp-edged end of the wiring since the ends of the wirings may be also integrated into the outer tubing.

Furthermore, the integration of the contacts in the connector enables the use of the dedicated medical equipment for the defined measuring or monitoring system. The dedicated connector may also be used as a connection point for the wiring to the monitor equipment or as a holder for a wireless transducer thus creating a visually wireless system.

Thus, a multiple wiring device can be made. The system is not limited to a two-wire-system since very thin wirings can be used because no isolation around the wires is needed. The electrodes and contacts can be of an inert metal totally harmless for the patient. This is useful since via the openings in the outer tubing there is a direct contact between the patient and the sensing elements. The feeding tube is not restricted to a simple lumen but may consist of a double lumen or a multi lumen tubing.

A feeding tube which meets the above-mentioned object and provides other beneficial features in accordance with the presently preferred exemplary embodiments of the invention will be described below with reference to FIGS. 1 to 4b,in which FIG. 1a shows a feeding tube according to the state of the art;

FIG. 1b shows a schematic view of a cross section of the wire being used in a feeding tube according to FIG. 1a;

FIG. 2b shows the outer tubing according to FIG. 2 mounted on to a feeding tube according to FIG. 1a;

FIG. 3b shows a schematic view of a wire mounting technique for a feeding tube according to FIG. 3a;

FIG. 4b depicts a schematic view of another embodiment of a feeding tube according FIG. 4a.

Figure 1A:
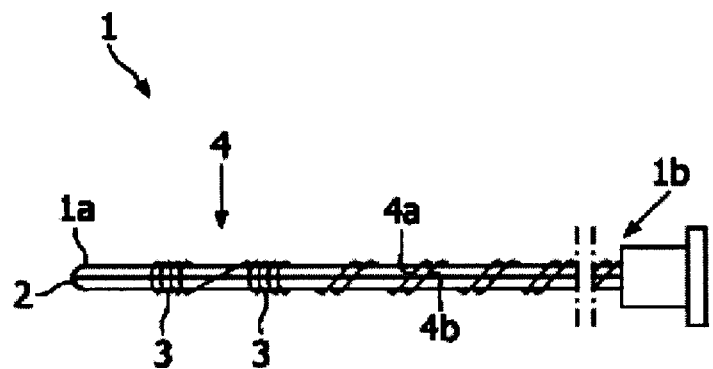

FIG. 1a shows a schematic view of a feeding tube 1 according to the state of the art. The feeding tube 1 shown in this embodiment is a single lumen feeding tube 1. It is of course possible to design the feeding tube 1 as a double lumen or multi lumen device. The lumen 2 in the center of the feeding tube 1 serves as supply for total parenteral nutrition or as a medicine dosing device for example for intensive care patients and immature babies. The feeding tube 1 is modified in that it allows an all-round monitoring of the vital parameters or other important parameters being self-evident in particular in intensive care treatment. Therefore, the feeding tube 1 includes a plurality of sensors interconnected to said feeding tube. The sensors are built by electrodes 3. In this embodiment around the feeding tube 1 at the location of the electrodes 3, an electrical wiring 4 is wound in a coil around the feeding tube 1 in a dense manner. In this embodiment the wiring 4 is built by two wires 4a and 4b. To connect the wiring 4 to the electronic circuit of the measuring or monitoring device the wiring 4 is spiral-wise wrapped around the feeding tube 1 towards its proximal end. With this a continuous wiring system is provided, which avoids the problems in connection with the contacting between the electrical wires 4a,4b and the electrodes 3 and between the wiring 4 and the electronic circuit of the monitoring device with otherwise is built by soldering the wires 4a, 4b to the electrodes 3 which may lead to a reliability problem.

Figure 1B:
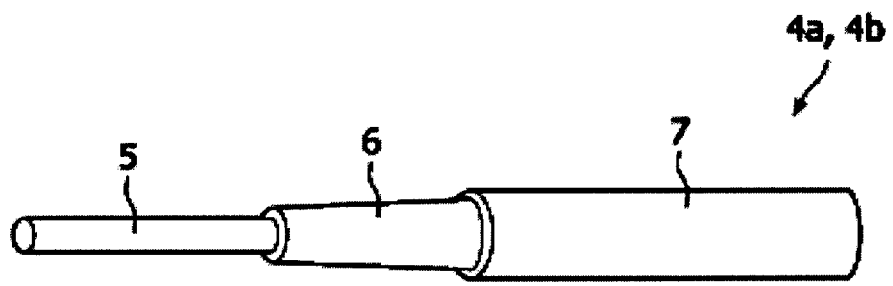

FIG. 1b shows a preferred embodiment of the wires 4a, 4b, building the wiring 4 of the feeding tube 1. The wires 4a, 4b are each composed of a core of a conductive metal 5 and a double isolation a layer 6, 7. The inner isolation layer 6 is used to isolate the wires 4a, 4b from each other to avoid a short circuit in case the two wires 4a, 4b coming in contact with each other for example by shifting when the feeding tube 1 is inserted into a patient's esophagus. The outer isolation layer 7 is used to protect the external wiring 4 to be connected to the measuring/monitoring device. This outer isolation layers 6, 7 will give the wiring 4 its mechanical strengths. At the location of the electrodes 3 the inner isolation layer 6 is removed from the wire 4a, 4b and the wires 4a,4b are tightly winded around the feeding tube 1.

In an embodiment not shown additionally electrodes are applied using a metal electrode or by using a conductive polymer, e.g. a polymer filed with conductive (metal) particles.

A problematic item of such a feeding tube 1 is that the wiring 4 is not protected against the outside world so that on one hand stress could be applied to the wiring 4 which may cause a reliability problem and the inner isolation layer 6 is exposed to the environmental condition which may lead to a dissolving of the insulation material being used so that the risk of a short circuit may be given if the material gets cavernous after sometime.

Therefore, the invention proposes to cover the wiring 4 on the feeding tube 1 by providing an outer tubing 8 in order to cover the feeding tube 1 according to FIG. 1a and/or the wiring 4. Because of providing the outer tubing the wiring 4 is isolated against the surrounding so that the material of the feeding tube 1—in the following being referred to as inner tubing 9—is free from any limitation regarding the material to be chosen because of an eventual allergic reaction of the patient. Furthermore, the risk of ageing of the material to be used because of the environmental conditions is minimized. A further advantage of such an outer tubing 8 is that it gives the wiring 4 as well as the inner tubing 9 a better mechanical strength and the risk of stress being applied to the wiring 4 is reduced.

Figure 2A:
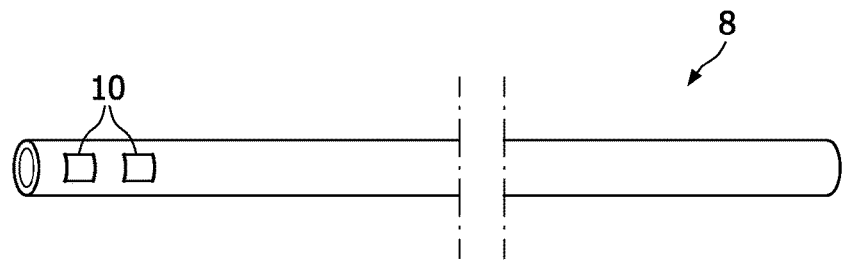
FIG. 2a depicts a schematic view of one embodiment of an outer tubing according to the invention.

To achieve all the above advantages, it is very important, that the outer tubing 8 is tightly fitted around the inner tubing 9. Therefore, in one embodiment the outer tubing 8 is designed as a shrinking-wrapping tube. Thus it gets very easy to first insert the inner tubing 9 into the shrinking tube according to this embodiment since before shrinking the inner diameter of the shrinking tube is bigger than the outer diameter of the inner tubing 9. Afterwards, the outer tubing 8 is treated in the way that it shrinks until it tightly fits around the inner tubing 9. As disclosed in FIG. 2a holes 10 are made in to the shrinking to exactly at the location of the electrodes 3 according to FIG. 1a to enable an access to the electrodes 3 for measuring the vital parameters to monitor a patient.

In an embodiment not shown the electrodes 3 are enlarged by applying an additional external electrode at each location of the winded electrodes 3 by depositing a thin metal film or by applying a highly conductive polymer e.g. by using a filled polymeric material.

A second way to mount the outer tubing with holes at the location of the electrodes is by stretching the inner tubing 9. In this embodiment the outer tubing 8 has a smaller inner diameter then the outer diameter of the inner tubing 9 wherein for insertion into the outer tubing 8 the inner tubing 9 may be stretched to diminish the outer diameter of the inner tubing temporarily ensuring a tight fit after release of the inner tubing 9.

To minimize the risk of a short circuit of the wiring 4 in one embodiment of the present invention (not shown) the inner tubing 9 is provided with at least one recess on its surface, that matches with the dimensions of the electrodes 3 and the wiring 4, to enable an easy positioning of the electrodes 3 and the wiring 4 at a location being determined by the location of recesses. This ensures that the electrodes 3 and the wiring 4 do not shift which otherwise may lead to a short circuit.

To enable an easy incubation of a patient the surface area of the outer tubing 8 may have a slight spiral shape. This enables a much smoother insertion of the feeding tube 1 compared to a completely flat outer surface. This shape can be actively manufactured into the surface before fixing the outer tubing 8 to the inner tubing 9. It is also possible that this structure may arise due to the close fitting of the inner tubing 9 and the outer tubing 8 because of the spiral wise wounded wiring 4 being located between the outer tubing 8 and the inner tubing 9. The occurrence of this spiral shape may either be influenced by the shrinking procedure of the outer tubing 8 or the difference between the inner diameter of the tubing 8 in relation with the outer diameter of the inner tubing 9.

Figure 2B:
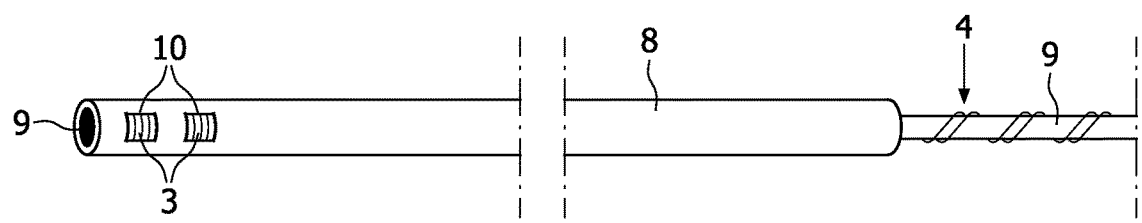

Since the feeding tube 1 according to FIG. 2 is build by two separate tubings, the inner tubing 9 and the outer tubing 8, two different materials may be used for the formation of each tubing 8, 9.

Figure 3A:
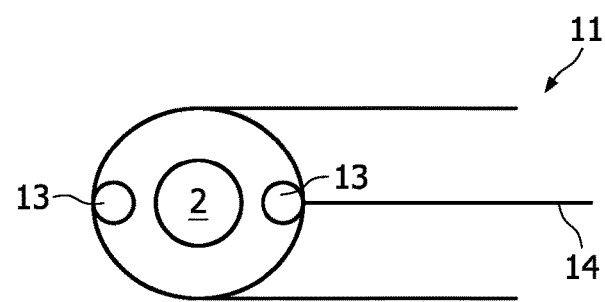
FIG. 3a shows an alternative embodiment of a feeding tube according to the invention comprising two outer lumens.

FIG. 3 shows an alternative embodiment of the present invention. In this embodiment a low cost manufactured feeding tube 11 is given which may be a single or multi lumen feeding tube 11. The feeding tube 11 has outer lumens 13 for guiding and protecting a wiring 12. In this embodiment the wiring 12 needs not to furnished with an isolating coating since the risk of the short circuit is very low since the several wirings 12 can be separated by the different lumens 13. Of course it is possible to provide as many lumens 13 as electrodes 3 are needed to accomplish the monitoring of a patient. The outer lumens 13 each provide the continuous opening 14 in the circumference of the feeding tube 11. Because of these openings 14 it is possible to insert the wiring 12 into the outer lumen 13 of the feeding tube 11 easily. Furthermore, it is also possible to exchange the wiring 12 even at the later stage. In this embodiment the outer tubing and the inner tubing are made from one-piece wherein the inner lumen 2 is formed in the center of the feeding tube 11 and two outer lumens 13 are formed near the surface of the one-piece feeding tube 11 as for guiding and protecting the wiring 12 to be inserted to the outer lumens 13.

Figure 3B:
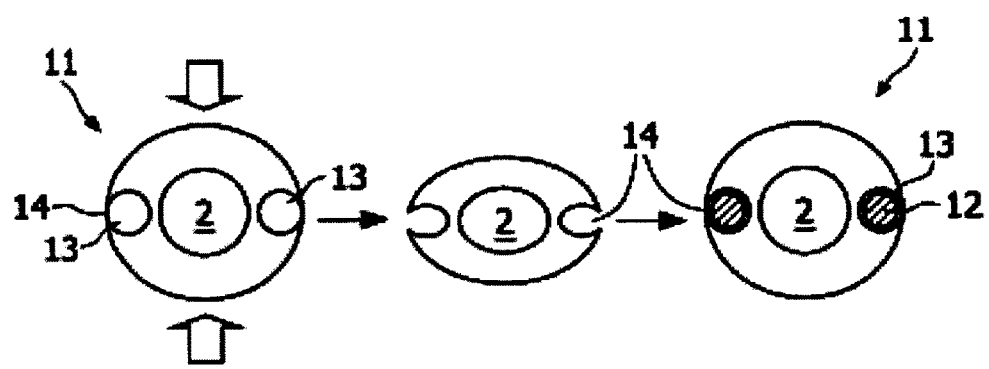

The material of the feeding tube 11 is flexible. Therefore, the insertion of the wiring 12 into the outer lumens 13 may be easily conducted by using a method which is schematically shown in FIG. 3b. For insertion of the wiring 12, the feeding tube 11 is pressed at the outside on the top and the bottom of the feeding tube 11 as indicated in FIG. 3b by two arrows. By pressing the outside of the feeding tube 11, the feeding tube 11 is deformed. This leads to a widening of the openings 14 on the surface of the feeding tube 11 thus enabling an easy positioning of the wiring 12 in the outer lumens 13 without any difficult technologies or even co extrusion of the wiring. The electrodes 3 are constructed by winding the wiring 12 into coils at designated locations onto the outside of the feeding tube 11. Summarizing one end of the wiring 12 is at the designated location of the electrodes 3 wound around the feeding tube 11 and its one end is inserted in the outer lumen 13 at the distal end of the feeding tube 11. The other end of the wiring 12 is connected to the measuring and/or monitoring equipment. To give the wiring 12 its mechanical strength the wiring 12 outside the feeding tube 11 in one embodiment compromises an additional electrical isolating material (not shown). Eventually, the wound wiring 12 building the electrodes 3 can additionally be over-coated by a conductive paint. In this construction no internal connections need to be made ensuring a high reliability of the device.

Figure 4A:
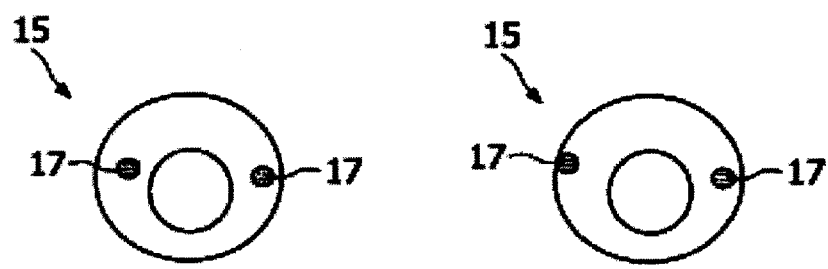
FIG. 4a shows a cross section of an alternative embodiment of a feeding tube made by injection molding for guiding and protecting the wiring.
Figure 4B:
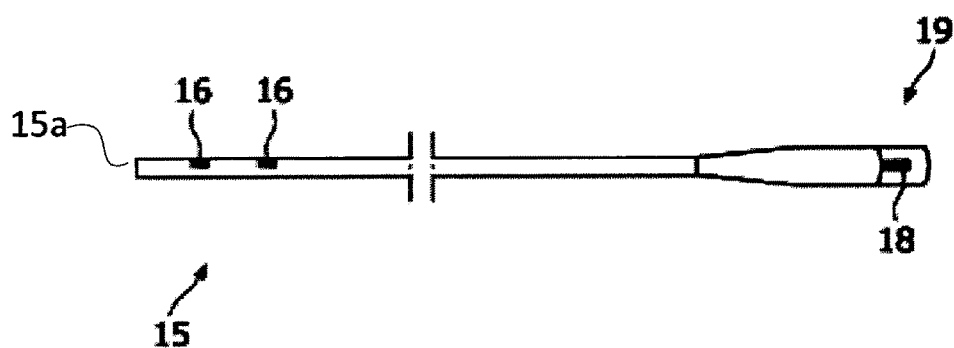

FIG. 4 shows a cross section of an alternative embodiment of a feeding tube 15 according to the invention. The feeding tube 15 is manufactured by injection molding which enables the integration of the active electrodes 16 at a distal end 15a of the feeding tube 15. The wiring 17, the electrodes 16 and a contacting there between are inserted in to the mould and afterwards are over-molded with the tubing material. Since the wiring 17 is completely included and protected in the material of the feeding tube 15, the use of very thin wiring 17 is possible because no isolation is needed and the integration of the contacts 18 to the measuring equipment in the feeding connector 19 of the being build by injection moulding is possible. Therefore, the integration of the connector 18 and the feeding tube 15 is possible. Furthermore, the distal end 15a of the feeding tube 15 is optimized in that the smoother end of the tubing 15a may be achieved by engineering the mould to be used. With this a possible harming of the patient due to one the end of the wirings 17 is prevented. The integration of the contacts 18 in the connector 19 enables the use of the dedicated medical equipment for the defined measuring system. The dedicated connector 19 (FIG. 4b) can be used as connection point for the contact 18 to the monitor or as a holder for a wireless transducer thus creating a visually wireless system. Because of the possibility of using very thin wiring 17 the system is not limited to a two-wire-system but rather to a multiple wire device.

In this embodiment the electrodes 16 and contacts 18 are of an inert metal alloy totally harmless for the patient. There are two ways of manufacturing the electrodes 16. First the electrodes 16 are manufactured and afterwards inserted into the mould to be over-moulded by injection moulding. Second, the electrodes 16 are formed during the moulding process itself by using a conductive material for example a filled polymeric material.

The material used for forming the tubing may be a polymer such as PVC, silicon or other polymeric material commonly used in the medical branch.

Those familiar with the state-of-the-art will appreciate that the description given herein with respect to those figures is for explanatory purposes only and is not intended to limit the scope of the invention.

The invention claimed is:

1. A feeding tube configured for insertion in an esophageal opening including:
   a flexible inner tubing including at least one lumen configured for parenteral nutrition and/or medicine dosing;
   at least one sensing element disposed along one end of an outside surface of the inner tubing and configured for internally sensing a patient's vital functions;
   electrically conductive wire connected to the at least one sensing element and to at least one monitoring device, and disposed on the outside surface of the inner tubing;
   an outer tubing which covers the inner tubing and the electrically conductive wire, a surface of the outer tubing having a spiral shape; and
   wherein the inner tubing has recesses pre-formed on the inner tubing surface that match with the dimensions of and receive the at least one sensing element and the wire.

2. The feeding tube according to claim 1, wherein the outer tubing includes a shrinkable tube which is shrunk fit over the inner tubing and wire by shrinking.

3. A feeding tube configured for insertion in an esophageal opening including:
   an inner tubing including at least one inner lumen configured for parenteral nutrition and/or medicine dosing and at least one outer lumen disposed adjacent an outside surface of the inner tubing with an opening extending continuously along the at least one outer lumen between the outer lumen and an outside surface of the inner tubing;
   at least one sensing element disposed adjacent one end on the outside surface of the inner tubing and configured for internally sensing a patient's vital functions;
   wire connected to the at least one sensing element and to at least one monitoring device, and disposed in the outer lumen of the inner tubing;
   an outer tubing which covers the inner tubing and the wire; and
   wherein the inner tubing is sufficiently flexible that radial pressure widens the opening to facilitate positioning the wire in the outer lumen.

4. The feeding tube according to claim 3, wherein the sensing element includes a coil of the wire on said inner tubing.

5. The feeding tube according to claim 3, wherein the inner and outer tubing are formed of a polymer.

6. The feeding tube according to claim 3, wherein the at least one sensing element includes an electrode, and the electrode includes at least one of:
   a thin metal film; or
   a highly conductive polymer.

7. The feeding tube according to claim 3, wherein the at least one sensing element includes an inert metal alloy.

8. A feeding tube, comprising:
   at least one sensing element which internally senses a patient's vital functions;
   wire connected to the at least one sensing element and to a contact;
   a tubing which includes a plurality of lumens, wherein a first lumen is formed in the center of the tubing and configured for feeding, and at least a second lumen formed between the first lumen and a surface of the tubing, and the wire being disposed in the second lumen, and the at least one sensing element being disposed on a surface of the tubing at a distal end of the tubing and the contact being disposed adjacent the opposite end of the tubing; and
   wherein at least one groove is defined in the second lumen, the tubing being flexible such that when the tubing is radially compressed, the groove provides a continuous opening between the second lumen and the surface of the tubing to enable a positioning of the wire in the second lumen from outside, the tubing being resilient such that when the tubing is not compressed, the opening is closed.

9. The feeding tube according to claim 8, wherein the at least one sensing element includes an electrode, and the electrode includes at least one of:
   a thin metal film; or
   a highly conductive polymer.

* * * * *